United States Patent
Ponzi

(10) Patent No.: US 7,905,864 B2
(45) Date of Patent: Mar. 15, 2011

(54) INJECTION CATHETER WITH MULTI-DIRECTIONAL DELIVERY INJECTION NEEDLE

(75) Inventor: Dean M. Ponzi, Glendora, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 0 days.

(21) Appl. No.: 10/414,624

(22) Filed: Apr. 16, 2003

(65) Prior Publication Data

US 2003/0171723 A1   Sep. 11, 2003

Related U.S. Application Data

(60) Division of application No. 09/562,611, filed on May 1, 2000, now Pat. No. 6,623,473, and a continuation-in-part of application No. 09/280,202, filed on Mar. 29, 1999, now Pat. No. 6,165,164.

(60) Provisional application No. 60/165,354, filed on Nov. 12, 1999, provisional application No. 60/088,019, filed on Jun. 4, 1998, provisional application No. 60/088,984, filed on Jun. 11, 1998.

(51) Int. Cl.
*A61M 5/178* (2006.01)

(52) U.S. Cl. .......... 604/164.02; 604/164.06; 604/164.11

(58) Field of Classification Search .............. 604/164.01–170.03, 198, 523, 604/95.01, 96, 272, 528, 96.01; 607/22; 606/41–52

See application file for complete search history.

(56) References Cited

U.S. PATENT DOCUMENTS

| | | |
|---|---|---|
| 3,598,119 A | 8/1971 | White |
| 4,006,744 A | 2/1977 | Steer |
| 4,201,387 A | 5/1980 | Revermann et al. |
| 4,270,535 A | 6/1981 | Bogue et al. |
| 4,391,199 A | 7/1983 | Morin |

(Continued)

FOREIGN PATENT DOCUMENTS

DE   19633406 A1   2/1998

(Continued)

OTHER PUBLICATIONS

Marshall, D.J. et al., "Biocompatibility of Cardiovascular Gene Delivery Catheters with Adenovirus Vectors: An Important Determinant of the Efficiency of Cardiovascular Gene Transfer", Molecular Therapy, vol. 1, No. 5, May 2000, Part 1 of 2 Parts, pp. 423-429.

(Continued)

*Primary Examiner* — Kevin C Sirmons
*Assistant Examiner* — Phillip Gray
(74) *Attorney, Agent, or Firm* — Christie, Parker & Hale, LLP

(57) ABSTRACT

An injection catheter is provided. The catheter comprises a catheter body comprising a flexible tubing having proximal and distal ends and at least one lumen therethrough. The catheter further comprises a tip section comprising a flexible tubing having proximal and distal ends, wherein the proximal end of the tip section is mounted at the distal end of the catheter body. A needle control handle is provided at the proximal end of the catheter body. An injection needle comprising elongated tubing extends through the tip section, catheter body, and needle control handle. The injection needle has a proximal end attached to the needle control handle, a distal region within the tip section, and an open distal end. The injection needle is longitudinally slidable within the tip section so that its distal region can extend beyond the distal end of the tip section upon suitable manipulation of the needle control handle. The distal region of the injection needle has at least one fluid port along its length. In use, fluid passes out of the needle through the open distal end and the at least one fluid port along the length of the distal region.

19 Claims, 9 Drawing Sheets

U.S. PATENT DOCUMENTS

| | | | |
|---|---|---|---|
| 4,397,314 A * | 8/1983 | Vaguine | 607/104 |
| 4,578,061 A | 3/1986 | Lemelson | |
| 4,966,597 A | 10/1990 | Cosman | |
| 5,042,486 A | 8/1991 | Pfeiler et al. | |
| 5,236,424 A | 8/1993 | Imran | |
| 5,244,460 A | 9/1993 | Unger et al. | |
| 5,333,622 A | 8/1994 | Casali et al. | |
| 5,336,222 A | 8/1994 | Durgin, Jr. et al. | |
| 5,354,279 A | 10/1994 | Hofling | |
| 5,364,352 A | 11/1994 | Cimino et al. | |
| 5,385,148 A | 1/1995 | Lesh et al. | |
| 5,391,199 A | 2/1995 | Ben-Haim | |
| 5,403,311 A | 4/1995 | Abele et al. | |
| 5,419,777 A | 5/1995 | Hofling | |
| 5,431,168 A | 7/1995 | Webster, Jr. | |
| 5,431,649 A * | 7/1995 | Mulier et al. | 606/41 |
| 5,435,805 A | 7/1995 | Edwards et al. | |
| 5,447,533 A | 9/1995 | Vachon et al. | |
| 5,464,395 A | 11/1995 | Faxon et al. | |
| 5,522,815 A * | 6/1996 | Durgin et al. | 606/50 |
| 5,531,780 A | 7/1996 | Vachon | |
| 5,588,432 A | 12/1996 | Crowley | |
| 5,599,294 A | 2/1997 | Edwards et al. | |
| 5,661,133 A | 8/1997 | Leiden et al. | |
| 5,725,524 A | 3/1998 | Mulier et al. | |
| 5,741,320 A | 4/1998 | Thornton et al. | |
| 5,779,647 A | 7/1998 | Chau et al. | |
| 5,797,870 A | 8/1998 | March et al. | |
| 5,810,804 A | 9/1998 | Gough et al. | |
| 5,833,715 A * | 11/1998 | Vachon et al. | 607/120 |
| 5,849,011 A | 12/1998 | Jones et al. | |
| 5,857,997 A | 1/1999 | Cimino et al. | |
| 5,876,340 A | 3/1999 | Tu et al. | |
| 5,891,138 A | 4/1999 | Tu et al. | |
| 5,893,885 A | 4/1999 | Webster | |
| 5,906,594 A | 5/1999 | Scarfone et al. | |
| 5,906,613 A | 5/1999 | Mulier et al. | |
| 5,921,978 A * | 7/1999 | Thompson et al. | 604/529 |
| 5,921,982 A * | 7/1999 | Lesh et al. | 606/41 |
| 6,102,887 A | 8/2000 | Altman | |
| 6,123,699 A | 9/2000 | Webster, Jr. | |
| 6,126,633 A | 10/2000 | Kaji et al. | |
| 6,165,164 A | 12/2000 | Hill et al. | |
| 6,171,277 B1 | 1/2001 | Ponzi | |
| 6,179,809 B1 | 1/2001 | Khairkhahan et al. | |
| 6,183,463 B1 | 2/2001 | Webster, Jr. | |
| 6,201,387 B1 | 3/2001 | Govari | |
| 6,238,389 B1 | 5/2001 | Paddock et al. | |
| 6,241,710 B1 | 6/2001 | VanTassel et al. | |
| 6,309,370 B1 | 10/2001 | Haim et al. | |
| 6,540,725 B1 | 4/2003 | Ponzi | |
| 6,575,931 B1 | 6/2003 | Ponzi | |
| 6,623,473 B1 | 9/2003 | Ponzi | |
| 6,623,474 B1 | 9/2003 | Ponzi | |
| 6,905,476 B2 | 6/2005 | Ponzi | |
| 2002/0183720 A1 | 12/2002 | Hill et al. | |
| 2002/0183738 A1 | 12/2002 | Chee et al. | |
| 2003/0171723 A1 | 9/2003 | Ponzi et al. | |
| 2003/0187396 A1 | 10/2003 | Ponzi | |
| 2003/0195470 A1 | 10/2003 | Ponzi | |

FOREIGN PATENT DOCUMENTS

| | | |
|---|---|---|
| DE | 19633406 A1 | 2/1998 |
| EP | 0826387 A2 | 3/1998 |
| EP | 0900549 A1 | 3/1999 |
| EP | 0900549 A1 | 3/1999 |
| EP | 0904796 A2 | 3/1999 |
| EP | 0908194 A2 | 4/1999 |
| EP | 0908194 A2 | 4/1999 |
| EP | 0962191 A1 | 12/1999 |
| EP | 0962191 A1 | 12/1999 |
| EP | 1 099 453 A2 | 5/2001 |
| EP | 0980226 B1 | 12/2005 |
| JP | 2-139649 | 11/1990 |
| JP | 3133429 A | 6/1991 |
| JP | 04022370 | 1/1992 |
| JP | 7088093 A | 4/1995 |
| JP | 8504613 T | 5/1996 |
| JP | 8510154 T | 10/1996 |
| JP | 9028664 A | 2/1997 |
| JP | 11239619 A | 9/1999 |
| WO | WO 94/26189 | 11/1994 |
| WO | WO 96/41654 A1 | 12/1996 |
| WO | WO 99/22655 | 5/1999 |
| WO | WO 99/22655 A1 | 5/1999 |
| WO | WO 00/35531 | 6/2000 |
| WO | WO 00/35531 A1 | 6/2000 |

OTHER PUBLICATIONS

Goette, A., M.D., et al; Transcatheter Subendocardial Infusion, A Novel Technique for Mapping and Ablation of Ventricular Myocardium, Circulation, vol. 94, No. 6, Sep. 1996, pp. 1449-1455.

Marshall, D. J. et al., Biocompatibility of Cardiovascular Gene Delivery Catheters with Adenovirus Vectors: An Important Determinant of the Efficiency of Cardiovascular Gene Transfer, Molecular Therapy, vol. 1, No. 5, May 2000, Part 1 of 2 Parts, pp. 423-429.

Ponzi, D., "Injection Catheter With Needle Electrode", U.S. Appl. No. 09/711,648, filed Nov. 13, 2000.

European Search Report dated May 7, 2004 for European Patent Application No. 03258245.4.

Goette, M.D., et al.; Transcatheter Subendocardial Infusion. A Novel Technique for Mapping and Ablation of Ventricular Myocardium; Circulation; Sep. 15, 1996; pp. 1449-1455; vol. 94, No. 6.

Marshall, et al.; Biocompatibility of Cardiovascular Gene Delivery Catheters with Adenovirus Vectors: An Important Determinant of the Efficiency of Cardiovascular Gene Transfer; Molecular Therapy; May 2000; pp. 423-429; vol. 1, No. 5, Part 1 of 2 Parts; The American Society of Gene Therapy.

Ponzi; Injection Catheter With Needle Electrode; Corresponding U.S. Appl. No. 09/711,648, filed Nov. 13, 2000.

* cited by examiner

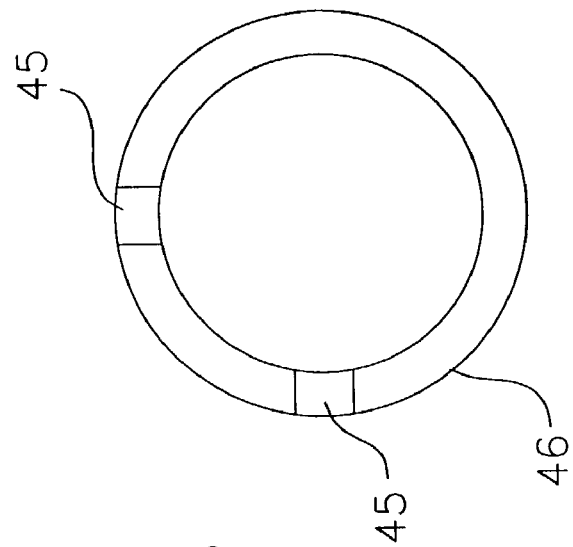
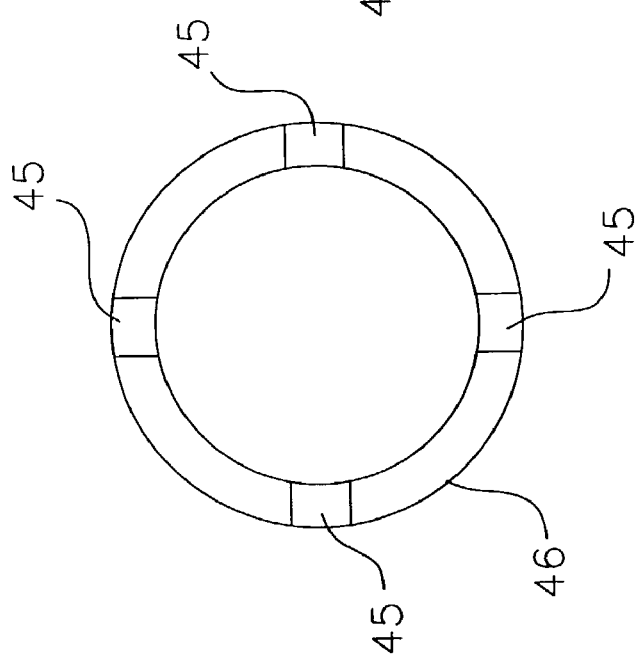
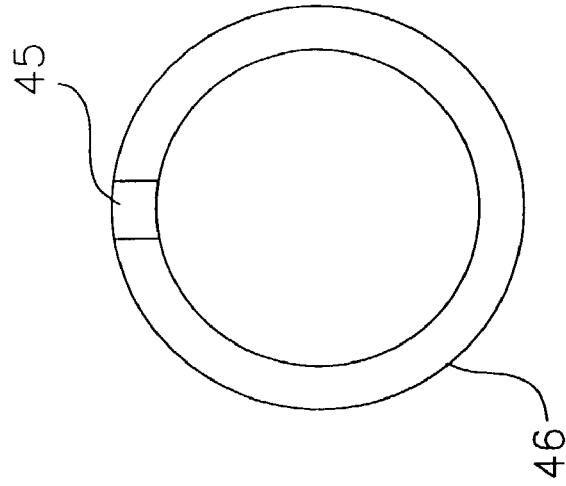

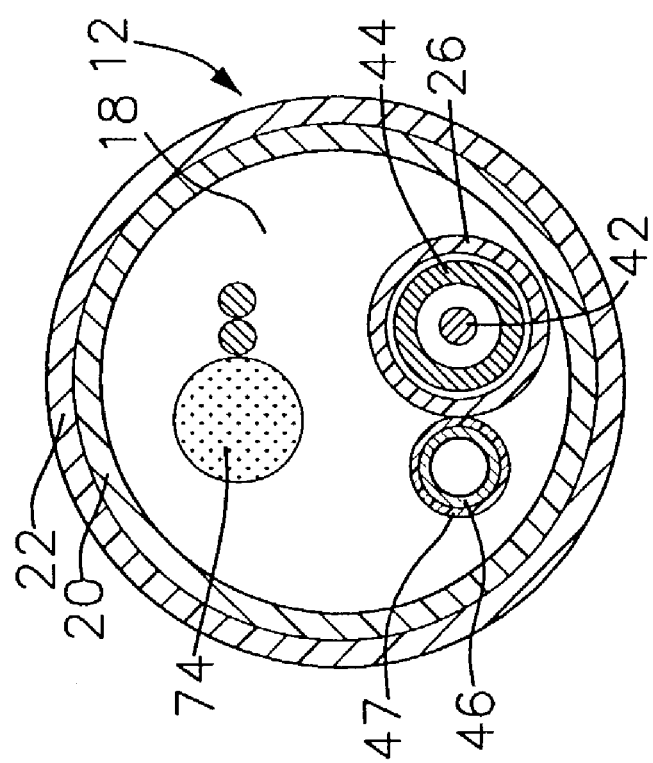
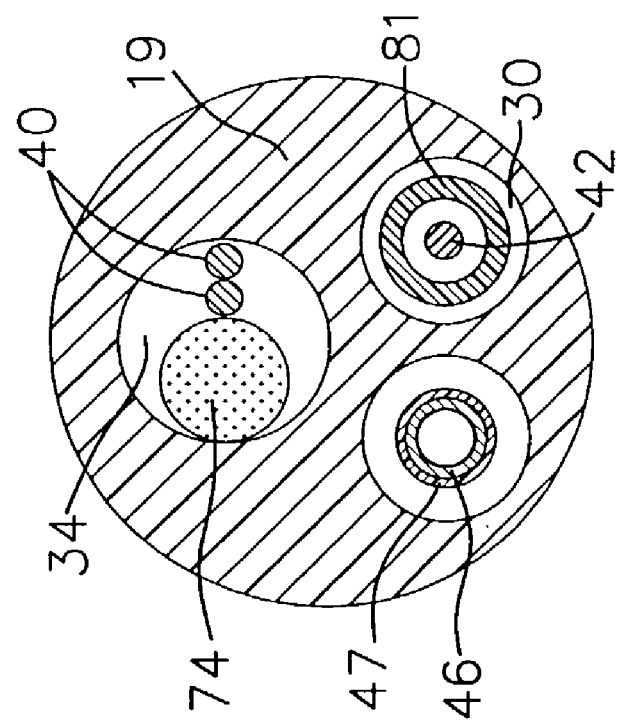

INJECTION CATHETER WITH MULTI-DIRECTIONAL DELIVERY INJECTION NEEDLE

CROSS-REFERENCE TO RELATED APPLICATIONS

This application is a divisional of U.S. patent application Ser. No. 09/562,611, filed May 1, 2000 now U.S. Pat. No. 6,623,473 which claims priority of U.S. Provisional Patent Application No. 60/165,354, filed Nov. 12, 1999, and is a continuation-in-part of U.S. patent application Ser. No. 09/280,202, filed Mar. 29, 1999 now U.S. Pat. No. 6,165,164, which claims priority of U.S. Provisional Patent Application Nos. 60/088,019, filed Jun. 4, 1998 and Ser. No. 60/088,984, filed on Jun. 11, 1998, the entire disclosures of which are incorporated herein by reference.

FIELD OF THE INVENTION

This invention relates to a catheter for infusing therapeutic or diagnostic agents into the tissue of organs having an injection needle that provides multi-directional drug delivery.

BACKGROUND OF THE INVENTION

Targeted delivery of therapeutic or-diagnostic agents, such as occurs in gene therapy, is very desirable but often presents a difficult challenge. A potential benefit of targeted delivery is that there is an increased efficiency obtained by the precise placement of the therapeutic agent. There are several problems to his procedure which must be overcome in order to obtain satisfactory results from such therapy, such as the problems of obtaining access to the delivery site, transporting the therapeutic agent to the desired site, injecting the therapeutic agent at the proper depth within the organ tissue, steering the distal end of the catheter to a desired location within the organ prior to infusing the agent, and positioning the distal tip of the catheter at precisely the same location where prior measurements have indicated that the drug should be infused. It is also important to for a physician to be able to monitor the position of the infusion needle with respect to the wall of the organ. In the case of an organ, such as the heart, in which the walls are in constant motion, the activity of positioning and monitoring the position of the distal tip of the catheter, or infusion needle, becomes especially difficult.

U.S. Pat. No. 3,598,119 discloses a medical device for injecting drugs in which the injection needle is guided through an inner lumen of a catheter for insertion of the needle under skin tissue. A bladder at the distal end of the catheter may be inflated through another lumen for holding the point of the needle point in a fixed position beneath the skin.

U.S. Pat. No. 4,578,061 discloses a catheter for injecting a liquid into a vein, or artery, through an injection needle which is longitudinally movable beyond the distal end of the catheter. A dual chamber system is utilized within the catheter tip to provide for movement of a plunger to extend the injection needle and also to allow for a plunger to be used to apply a predetermined dose of medication through the injection needle.

U.S. Pat. No. 4,578,061 discloses an injection catheter having a longitudinal movable needle which may be moved through a lumen in order to extend out of the side wall of the catheter for injecting a liquid into a blood vessel. The needle is normally retracted into the device so that the needle will not penetrate tissue as the device is moved through a body duct. Thereafter, the needle is moved out of the side of the catheter into a vessel wall in order to infuse a liquid into the wall of a vessel.

U.S. Pat. No. 5,244,460 is directed toward a method for improving blood flow to the heart. More particularly this patent is directed toward a medical procedure for improving the growth of cardiac blood vessels by inserting a catheter into a coronary artery and injecting into the heart a blood vessel growth promoting peptide through an injection port of the catheter.

U.S. Pat. No. 5,419,777 is directed toward a catheter for injection of a fluid into body cavities such as coronary vessels and arteries. This patent, as is the case with the '061 patent, illustrates the use of an injection needle which protrudes laterally through the side walls of the distal tip of the catheter. In the case of drug injections to be made into coronary vessels and arteries, it is very desirable to have the needles extend out of the side walls of the catheter and at an acute angle to the walls of the vessel in order to penetrate the walls of the vessel for injection of the agent.

U.S. Pat. No. 5,431,168, assigned to the same assignee as the present patent application, is directed toward a steerable catheter which includes a puller wire for controlling the distal end of the catheter from a control handle which is mounted on the proximal end of the catheter.

Copending U.S. patent application Ser. No. 09/019,453, entitled "Intracardiac Drug Delivery," assigned to an affiliated company of the assignee of this application, discloses an injection catheter system for infusing a diagnostic or therapeutic agent into the wall of an organ which includes an electromagnetic sensor disposed within the distal tip of the catheter for providing very precise location information for the distal tip of the catheter. The subject matter of this copending patent application is incorporated by reference into the subject patent application.

Copending U.S. patent application Ser. No. 09/280,202 describes an injection catheter with an injection needle that has a passage therethrough, whereby a therapeutic agent is administered through the distal end of the needle. However, the efficiency at which the catheter delivers the drug is very important. One of the most difficult problems with therapeutic angiogenesis is getting the drug or other agent to properly absorb into the heart muscle to maximize its effect. If the drug is not properly injected and absorbed into the muscle, it may promote the growth of cancer cells or the spread of preexisiting cells throughout the body. It is undesirable to grow new blood vessels in certain parts of the body, such as the eyes or the kidneys.

SUMMARY OF THE INVENTION

This present invention is directed to a catheter for infusing therapeutic or diagnostic agents into the tissue of organs having an improved injection needle that provides multidirectional delivery. This design helps distribute a drug or other therapeutic agent more evenly into the heart muscle.

In accordance with the invention, the catheter comprises a catheter body comprising a flexible tubing having proximal and distal ends and at least one lumen therethrough. The catheter further comprises a tip section comprising a flexible tubing having proximal and distal ends, wherein the proximal end of the tip section is mounted at the distal end of the catheter body. A needle control handle is provided at the proximal end of the catheter body. An injection needle comprising elongated tubing extends through the tip section, catheter body, and needle control handle. The injection needle has a proximal end attached to the needle control handle, a distal region within the tip section, and an open distal end. The injection needle is longitudinally slidable within the tip section so that its distal region can extend beyond the distal end of the tip section upon suitable manipulation of the needle control handle. The distal region of the injection needle has at least one fluid port along its length. In use, fluid passes out of the needle through the open distal end and the at least one fluid opening along the length of the distal region.

DESCRIPTION OF THE DRAWINGS

These and other features and advantages of the present invention will be better understood by reference to the following detailed description when considered in conjunction with the accompanying drawings wherein:

FIGS. 3A, 3B, and 3C are end cross-sectional views of alternative embodiments of injection needles in accordance with the invention.

FIG. 6 is a transverse cross-sectional view of the tip section of FIG. 3 along line 6-6 showing an embodiment having three lumens.

FIG. 7 is a transverse cross-sectional view of the catheter body along line 7-7.

DETAILED DESCRIPTION

Figure 1:
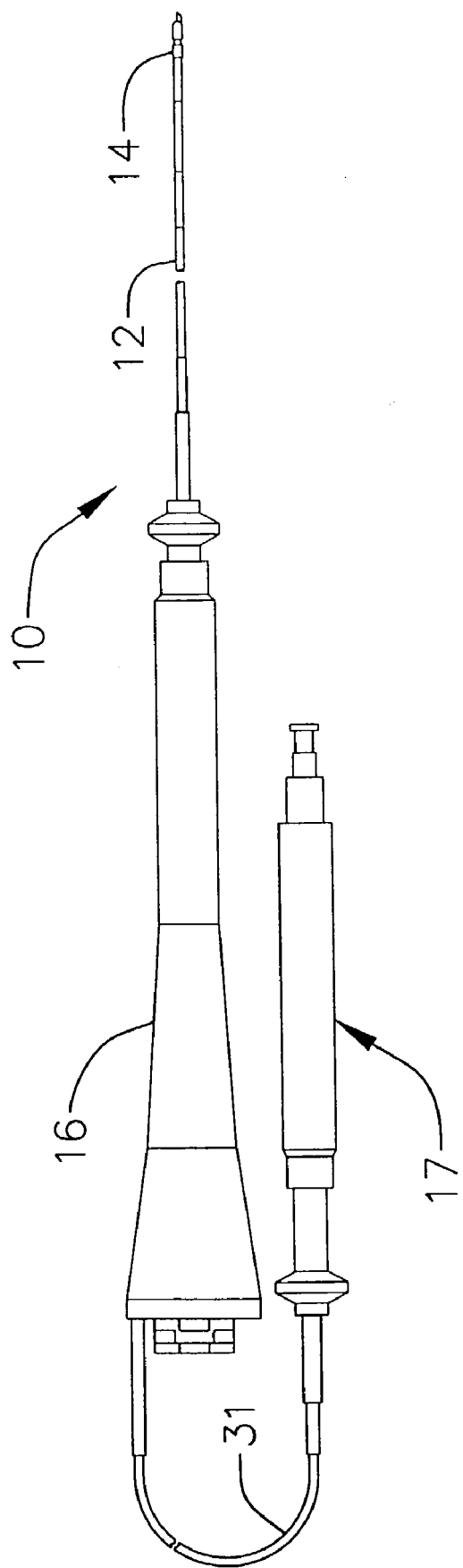
FIG. 1 is a side plan view of one embodiment of the catheter of the present invention.

In a preferred embodiment of the invention, there is provided a catheter for use for injection of a therapeutic or diagnostic agent into the heart. As shown in FIG. 1, catheter 10 comprises an elongated catheter body 12 having proximal and distal ends, a tip section 14 at the distal end of the catheter body 12, a deflection control handle 16 at the proximal end of the catheter body 12, and a needle control handle 17 proximal the catheter body.

Figure 5:
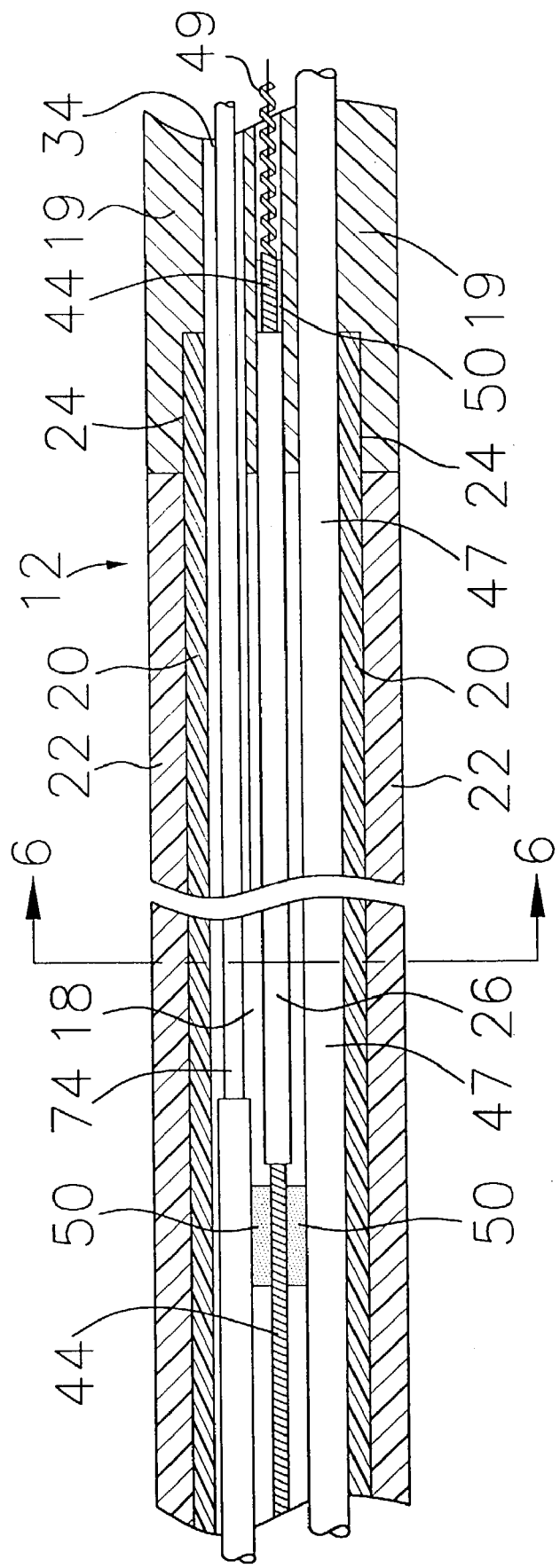
FIG. 5 is a side cross-sectional view of the catheter body, including the junction between the catheter body and the section.

With reference to FIGS. 5 and 7, the catheter body 12 comprises a single, central or axial lumen 18. The catheter body 12 is flexible, i.e., bendable, but substantially non-compressible along its length. The catheter body 12 may be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide.

The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used. If desired, the stiffening tube 20 can be eliminated.

Figure 3:
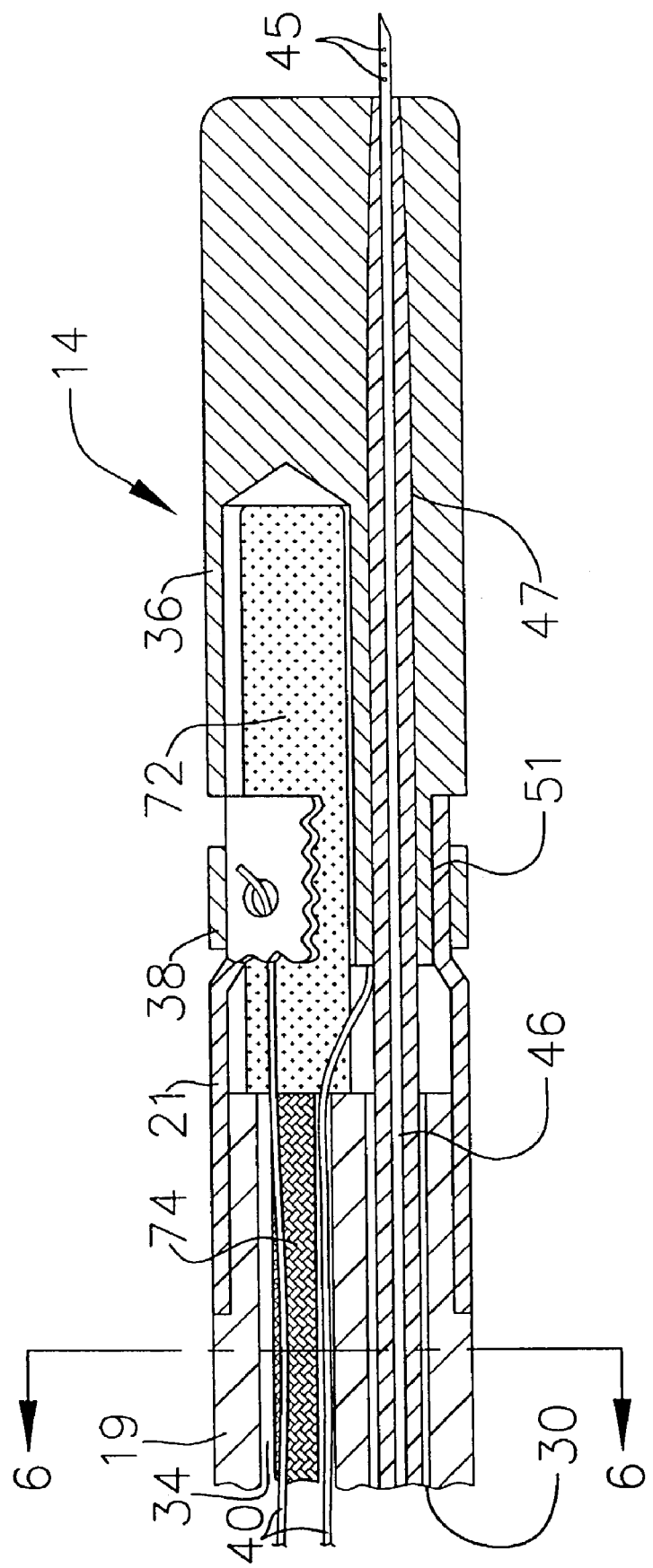
FIG. 3 is a side cross-sectional view of a tip section according to the invention having three lumens, showing the position of the electromagnetic mapping sensor and the injection needle.
Figure 4:
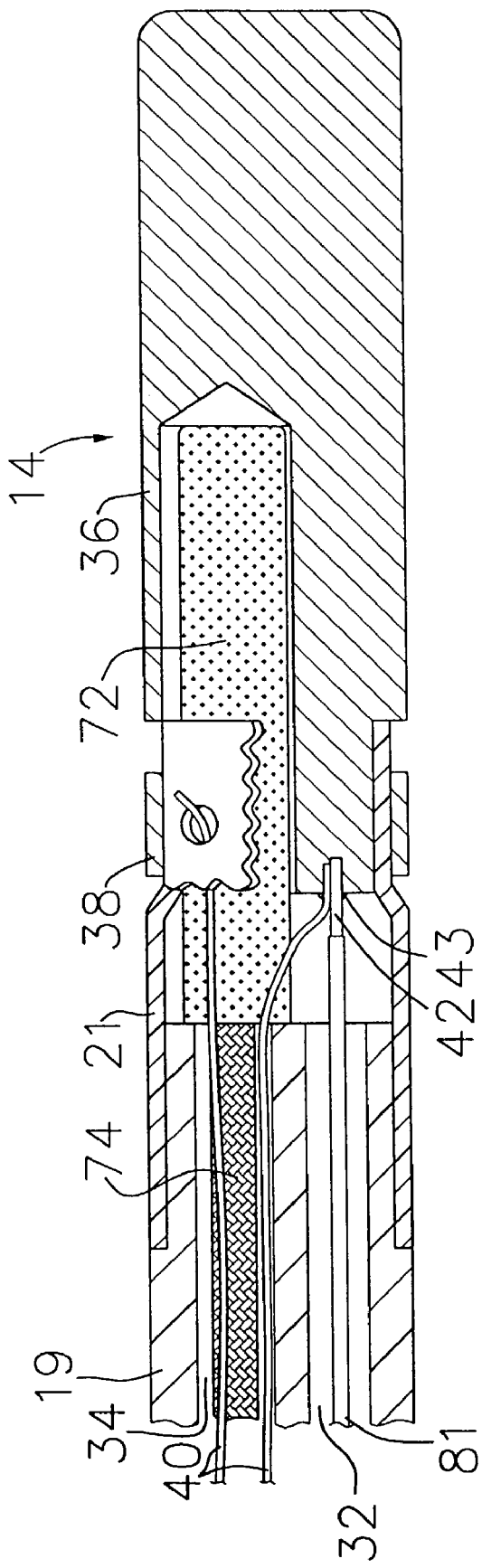
FIG. 4 is a side cross-sectional view of the tip section of FIG. 3 showing the position of the electromagnetic mapping sensor and the puller wire.

As shown in FIGS. 3, 4 and 6, the tip section 14 comprises a short section of tubing 19 having three lumens 30, 32 and 34. The tubing 19 is made of a suitable non-toxic material which is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 French. The size of the lumens is not critical. In a particularly preferred embodiment, the tip section has an outer diameter of about 7 French (0.092 inch) and the first lumen 30 and second lumen 32 are generally about the same size, having a diameter of about 0.022 inch, with the third lumen 34 having a slightly larger diameter of about 0.036 inch.

A preferred means for attaching the catheter body 12 to the tip section 14 is illustrated in FIG. 5. The proximal end of the tip section 14 comprises an inner counter bore 24 that receives the outer surface of the polyimide stiffener 20. The tip section 14 and catheter body 12 are attached by glue or the like.

The stiffening tube 20 is held in place relative to the outer wall 22 at the proximal end of the catheter body 12. In preferred construction of the catheter body 12, a force is applied to the proximal end of the stiffening tube 20 which causes the distal end of the stiffening tube 20 to firmly push against the counter bore 24. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane. Any other suitable method of attaching the catheter body 12 to the tip section 14 can be used.

Extending through the single lumen 18 of the catheter body 12 are lead wires 40, an injection needle 46, a sensor cable 74, and a compression coil 44 through which a puller wire 42 extends. A single lumen 18 catheter body is preferred over a multi-lumen body because it has been found that the single lumen 18 body permits better tip control when rotating the catheter 10. The single lumen 18 permits the lead wires 40, the injection needle 46, the sensor cable 74, and the puller wire 42 surrounded by the compression coil 44 to float freely within the catheter body. If such wires and cables were restricted within multiple lumens, they tend to build up energy when the handle 16 is rotated, resulting in the catheter body 12 having a tendency to rotate back if, for example, the handle is released, or if bent around a curve, to flip over, either for which are undesirable performance characteristics.

With reference to FIGS. 3 and 4, mounted at the distal end of the tip section 14 is a tip electrode 36. Preferably the tip electrode 36 has a diameter about the same as the outer diameter of the tubing 19. The tip electrode 36 is connected to the tubing 19 by means of a plastic housing 21, preferably made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14. Alternatively, the tip electrode 36 can be mounted directly to the distal end of the flexible tubing 19 of the tip section 14.

Mounted on the distal end of the plastic housing 21 is a ring electrode 38. The ring electrode 38 is slid over the plastic housing 21 and fixed in place by glue or the like. If desired, additional ring electrodes may be used and can be positioned over the plastic housing 21 or over the flexible tubing 19 of the tip section 14.

The tip electrode 36 and ring electrode 38 are each connected to a separate lead wire 40. The lead wires 40 extend through the third lumen 34 of tip section 14, the catheter body 12, and the control handle 16, and terminate at their proximal end in an inputjack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wires 40 are attached to the tip electrode 36 and ring electrode 38 by any conventional technique. Connection of lead wire 40 to the tip electrode 36 is preferably accomplished by weld 43, as shown in FIG. 4.

A puller wire 42 is provided for deflection of the tip section 14. The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

As discussed above, a compression coil 44 is provided in surrounding relation to a portion of the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40, injection needle 46 or sensor cable 74. A nonconductive sheath 26 made of polyimide tubing is presently preferred.

The compression coil 44 is anchored at its proximal end to the proximal end of the stiffening tube 20 in the catheter body 12 by glue to form a glue joint 50 and at its distal end to the tip section 14 in the second lumen 32, also forming a glue joint 50. The glue may be applied by means of a syringe or the like through a hole made between the outer surface of the catheter body 12 and the single lumen.

The puller wire 42 extends into the second lumen 32 of the tip section 14. The distal end of the puller wire 42 is anchored to the tip electrode 36 or to the side of the catheter tip section 14. With reference to FIGS. 4 and 5, within the tip section 14, and distal to the glue joint 50, the turns of the compression coil are expanded longitudinally. Such expanded turns 49 are both bendable and compressible and preferably extend for a length of about 0.5 inch. The puller wire 42 extends through the expanded turns 49 then into a plastic, preferably Teflon®, sheath 81, which prevents the puller 42 from cutting into the wall of the tip section 14 when the section 14 is deflected.

An injection needle 46 is provided, which comprises an elongated tubing including an internal bore defined by the inner annular surface of the tubing. The injection needle 46 extends from the needle control handle through the catheter body 12, through the first lumen 30 of the tip section 14 and through a passage 51 in the tip electrode 36. As illustrated in FIG. 3, the injection needle 46 is preferably formed with a beveled edge at the distal end of the needle. The needle 46 is coaxially mounted within a protective tube 47, preferably made of polyimide, which serves to prevent the needle from buckling and also serves to electrically insulate the needle from the distal electrode 36. The protective tube 47 additionally serves to provide a fluid-tight seal surrounding the injection needle 46.

The injection needle has a distal region that is maintained within the tip section 14, including the tip electrode 36, and that is extendable beyond the distal end of the tip section. FIG. 3 depicts the distal region of the injection needle 46 extending beyond the distal end of the tip electrode 36, as it would be positioned in order to infuse diagnostic or therapeutic fluid into the human heart. The distal region of the injection needle 46 is withdrawn into the tip section 14, including the tip electrode 36 if provide, during the period of time that the catheter is inserted through the vasculature of the body and also during the period of time in which the catheter is removed from the body to avoid injury. Alternatively, the tip section 14 can be provided without a tip electrode 36, in which case the distal end of the injection needle 46 could be retracted into the first lumen 30 of the tip section 14. In either embodiment, the injection needle 46 is extendable and retractable beyond the distal end of the catheter. If desired, the catheter can include a needle stop mechanism for limiting the distance that the needle extends beyond the distal end of the tip section 14. Such a mechanism is described in copending U.S. Patent Application entitled "Injection Catheter with Needle Stop" to Dean Ponzi, filed on even date herewith, the entire disclosure of which is incorporated herein by reference.

The elongated tubing that forms the injection needle 46 can be made from a single piece of tubing or a plurality of pieces of tubing connected together at their ends, which can be made from the same material or different materials. In one embodiment, the injection needle 46 is made from a single piece of Nitinol tubing. Other suitable materials for the tubing are described in copending U.S. Patent Application entitled "Catheter with Injection Needle" to Dean Ponzi, filed on even date herewith, the entire disclosure of which is incorporated herein by reference. Preferably the elongated tubing forming injection needle 46 has an inner diameter ranging from about 0.007 inch to about 0.011 inch, and an outer diameter ranging from about 0.012 inch to about 0.016 inch. Preferably the injection needle 46 has a total length ranging from about 65 to about 85 inches, more preferably about 75 inches.

The distal end of the injection needle 46 is open so that fluids, such as drugs and other agents, such as therapeutic or diagnostic agents, can pass through the internal bore of the needle and out the distal end. Additionally, the distal region of the injection needle 46, i.e., that portion of the needle that is extendable beyond the distal end of the tip section 14, is provided with one or more fluid ports 45 along its length, through which fluid can also pass. The fluid ports 45 can be of any suitable shape, such as round, oval, or rectangular (e.g., vertical or horizontal slots), and can be formed by any suitable method, such as by laser drilling. The fluid ports 45 can be provided on only one side of the needle 46, as shown in FIG. 3A, about the circumference of the needle, as shown in FIG. 3B, or only on selected sides of the needle, as shown in FIG. 3C. Preferably at least 3 fluid ports are provided, more preferably at least 5 fluid ports are provided. Preferably each fluid port 45 has a length ranging from about 0.005 inch to about 0.04 inch, more preferably about 0.02 inch. In a particularly preferred embodiment, four fluid ports are provided, with the most distal fluid port positioned a distance of about 2 inches from the distal end of the needle, and with a distance of about 0.02 inch provided between the fluid ports. In this preferred embodiment, two fluid ports are provided on one side of the needle, with the other two fluid ports on the opposite side of the needle. The fluid ports 45 enhance the ability of the drug or other agent passing through the needle to weep into the injection side and be more evenly distributed, allowing for better absorption of the agent by the heart tissue.

Additionally, an electromagnetic sensor 72 is contained within the distal end of the tip section 14. The electromagnetic sensor 72 is connected to an electromagnetic sensor cable 74, which extends through the third lumen 34 of the tip section 14 through the catheter body 12 into the control handle 16. The electromagnetic sensor cable 74 comprises multiple wires encased within a plastic sheath. In the control handle 16, the wires of the sensor-cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. Suitable electromagnetic sensors for use in connection with the present invention are described, for example, in U.S. Pat. No. 4,391,199 and U.S. patent application Ser. No. 09/160,063, entitled "Miniaturized Position Sensor," the disclosures of which are incorporated herein by reference. A preferred electromagnetic mapping sensor 72 is manufactured by Biosense Webster, Inc. and marketed under the trade designation NOGA. To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the injection catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of the catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved.

The electromagnetic mapping sensor 72 can be used alone or more preferably in combination with the tip electrode 36 and ring electrode 38. By combining the electromagnetic sensor 72 and electrodes 36 and 38, a physician can simultaneously map the contours or shape of the heart chamber, the electrical activity of the heart, and the extent of displacement of the catheter and hence identify the presence and location of the ischemic tissue. Specifically, the electromagnetic mapping sensor 72 is used to monitor the precise location of the tip electrode in the heart and the extent of catheter displacement. The tip electrode 36 and ring electrode 38 are used to monitor the strength of the electrical signals at that location. Healthy heart tissue is identified by strong electrical signals in combination with strong displacement. Dead or diseased heart tissue is identified by weak electrical signals in combination with dysfunctional displacement, i.e., displacement in a direction opposite that of healthy tissue. Ischemic, or hibernating or stunned, heart tissue is identified by strong electrical signals in combination with impaired displacement. Hence, the combination of the electromagnetic mapping sensor 72 and tip and ring electrodes 36 and 38 is used as a diagnostic catheter to determine whether and where to infuse a drug into the wall of the heart. Once the presence and location of ischemic tissue has been identified, the tip section 14 of the catheter can be deflected so that the injection needle 46 is generally normal, i.e., at a right angle, to the ischemic tissue, and the injection needle may then be extended out of the distal end of the tip electrode 36 and into the wall of the heart.

It is understood that, while it is preferred to include both electrophysiology electrodes and an electromagnetic sensor in the catheter tip, it is not necessary to include both. For example, an injection catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Biosense Webster, Inc., and means for monitoring and displaying the signals received from the electrodes and electromagnetic sensor, such as the Biosense-NOGA system, also marketed by Biosense Webster, Inc.

The electrode lead wires 40 and electromagnetic sensor cable 74 must be allowed some longitudinal movement within the catheter body so that they do not break when the tip section 14 is deflected. To provide for such lengthwise movement, there is provided a tunnel through the glue joint 50, which fixes the proximal end of the compression coil 44 inside the catheter body 12. The tunnel is formed by a transfer tube 27, preferably made of a short segment of polyimide tubing. Preferably the transfer tube is approximately 60 mm long and has an outer diameter of about 0.021 inch and an inner diameter of about 0.019 inch.

Figure 8:
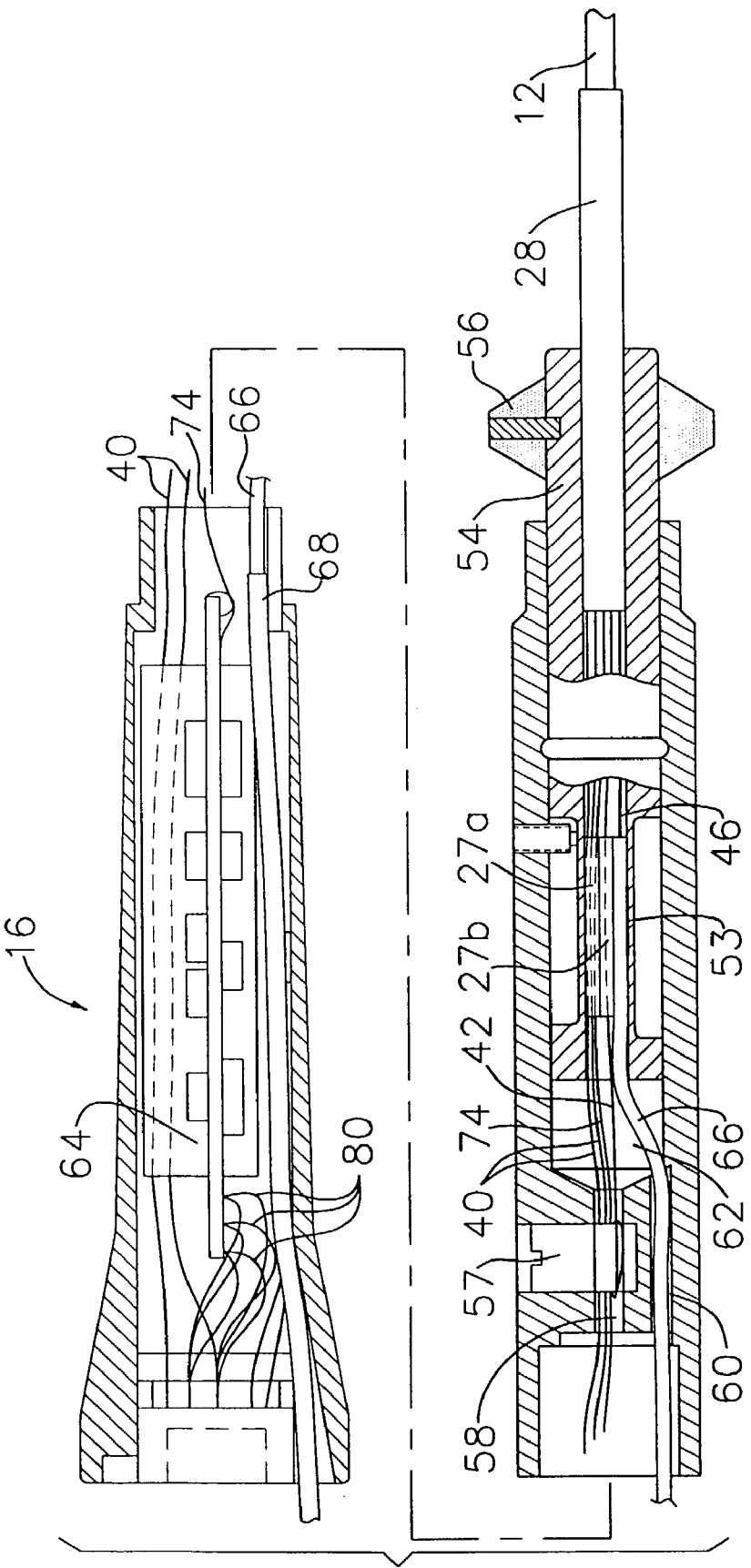
FIG. 8 is a side cross-sectional view of the catheter handle.

Longitudinal movement of the puller wire 42 relative to the catheter body 12, which results in deflection of the tip section 12, is accomplished by suitable manipulation of the control handle 16. As shown in FIG. 8, the distal end of the control handle 16 comprises a piston 54 with a thumb control 56 for manipulating the puller wire 42. The proximal end of the catheter body 12 is connected to the piston 54 by means of a shrink sleeve 28.

The injection needle 46 within the protective tube 47, the puller wire 42, the lead wires 40 and the electromagnetic sensor cable 74 extend through the piston 54. The puller wire 42 is anchored to an anchor pin 57 located proximal to the piston 54. The lead wires 40 and electromagnetic sensor cable 74 extend through a first tunnel 58, located near the side of the control handle 16. The electromagnetic sensor cable 74 connects to the circuit board 64 in the proximal end of the control handle. Wires 73 connect the circuit board 64 to a computer and imaging monitor (not shown).

The injection needle 46 and protective tube 47 extend through a guide tube 66, preferably made of polyurethane, and are afforded longitudinal movement therein. The guide tube 66 is anchored to the piston 54, preferably by glue at glue joint 53. This design allows the needle 46 and protective tube 47 longitudinal movement within the control handle 16 so that the needle 46 does not break when the piston 54 is adjusted to manipulate the puller wire 42. Within the piston 54, the electromagnetic sensor cable 74 and lead wires 40 are situated within a transfer tube 27a, and the puller wire 42 is situated within another transfer tube 27b to allow longitudinal movement of the wires and cable near the glue joint 53.

The injection needle 46, protective tube 47 and guide tube 66 extend through a second tunnel 60 situated near the side of the control handle 16 opposite the anchor pin 36. To avoid undesirable bending of the injection needle 46, a space 62 is provided between the proximal end of the piston 54 and the distal end of the second tunnel 60. Preferably the space 62 has a length of at least 0.50 inch and more preferably about from about 0.60 inch to about 0.90 inch.

In the proximal end of the control handle 16, the injection needle 46, protective tube 47 and polyurethane guide tube 66 extend through a second larger plastic guide tube 68, preferably made of Teflon®, which affords the guide tube 66, injection needle 46, and protective tube 47 longitudinal slidable movement. The second guide tube 68 is anchored to the inside of the control handle 16 by glue or the like and extends proximally beyond the control handle 16. The second guide tube 68 protects the injection needle 46 both from contact with the circuit board 64 and from any sharp bends as the guide tube 66, needle 46, and protective tube 47 emerge from the control handle 16.

Figure 2A:
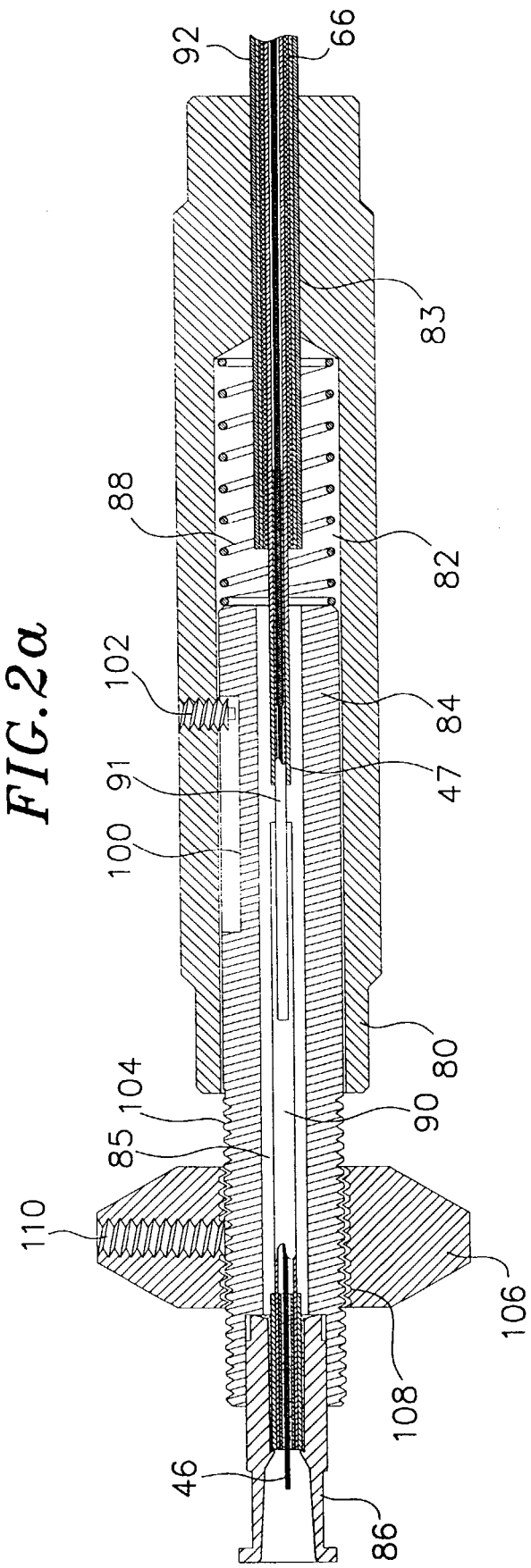
FIG. 2a is a side cross-sectional view of the needle control handle where the needle is in a retracted position.
Figure 2B:
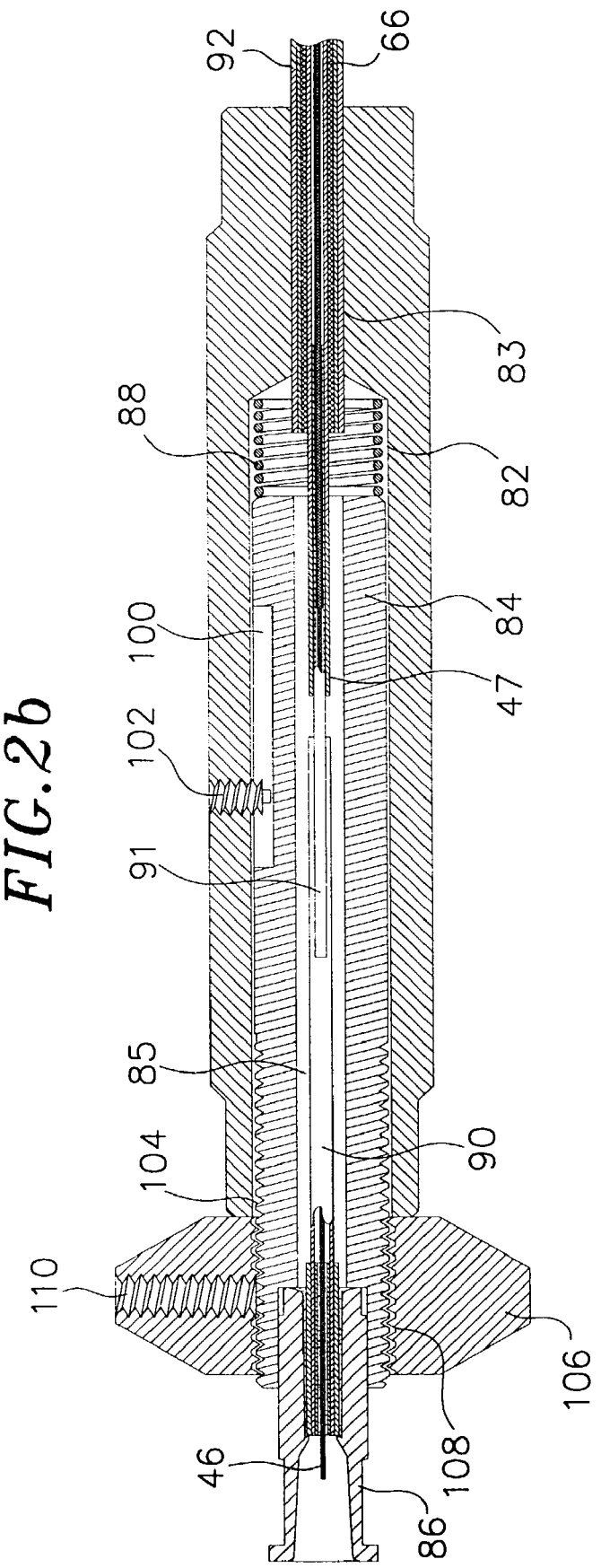
FIG. 2b is a side cross-sectional view of the needle control handle where the needle is in an extended position.

Extension and retraction of the injection needle 46 out the distal end of the tip electrode 36 is accomplished by the needle control handle 17. As illustrated in FIGS. 2a and 2b, the needle control handle 17 comprises a generally cylindrical outer body 80 having proximal and distal ends, a piston chamber 82 extending a part of the way therethrough, and a needle passage 83 extending a part of the way therethrough. The piston chamber 82 extends from the proximal end of the handle part way into the body 80, but does not extend out the distal end of the body. The needle passage 83, which has a diameter less than that of the piston chamber 82, extends from the proximal end of the piston chamber to the proximal end of the outer body 80.

A piston 84, having proximal and distal ends, is slidably mounted within the piston chamber 82. A Luer connector 86 is mounted in the distal end of the outer body. The piston 84 has an axial passage 85 through which the injection needle 46 extends, as described in more detail below. A compression spring 88 is mounted within the piston chamber 82 between the distal end of the piston 84 and the outer body 80.

The proximal end of the injection needle 46 is mounted to the Luer connector 86 by means of a first rigid tube 90, preferably made of stainless steel, which has a proximal end fitted into the Luer connector. This arrangement fixedly attaches the injection needle 46 to the piston 84 so that it moves longitudinally with the piston. The first rigid tube 90 is also fixedly attached to the piston 84 and moves longitudinally with the piston. The injection needle 46 and first rigid tube 90 extend through the axial passage 85 of the piston 84. Within the axial passage 85, a second rigid tube 91, preferably made of stainless steel, has a proximal end mounted coaxially within the distal end of the first rigid tube 90. The proximal end of the second rigid tube 91 is mounted within the protective tube 47, which has its proximal end inside the axial passage 85, and the distal end of the second rigid tube is attached, directly or indirectly, to the outer body 80. The guide tube 66, through which the protective tube 47 and injection needle 46 extend, as discussed above, is fixedly attached to the outer body 80 by means of a shrink sleeve 92, as is generally known in the art.

In use, force is applied to the piston 84 to cause distal movement of the piston relative to the outer body 21, which compresses the compression spring 88. This movement causes the injection needle 46 to correspondingly move distally relative to the outer body, guide tube 66, protective tube 47 and catheter body 12, so that the distal end of the injection needle extends outside the distal end of the tip electrode 36. When the force is removed from the piston, the compression spring 88 pushes the piston 84 proximally to its original position, thus causing the distal end of the injection needle 46 to retract back into the tip electrode 36. Upon distal movement of the piston 84, the first rigid tube 91 moves distally over the second rigid tube 91 to prevent the injection needle 46 from buckling within the axial passage 85.

The piston 84 further comprises a longitudinal slot 100 extending along a portion of its outer edge. A set screw 102 extends through the outer body 80 and into the longitudinal slot 100. This design limits the distance that the piston can be slid proximally out of the piston chamber 82. When the distal end of the injection needle 46 is in the retracted position, preferably the set screw 102 is at or near the distal end of the longitudinal slot 100.

The proximal end of the piston 84 has a threaded outer surface 104. A circular thumb control 106 is mounted on the proximal end of the piston. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the injection needle 46 can be extended out the distal end of the catheter. The threaded surfaces of the thumb control 106 and piston 84 allow the thumb control to be moved closer or farther from the proximal end of the outer body 80 so that the extension distance of the injection needle can be controlled by the physician. A tension screw 110 is provided in the thumb control 106 to control the tension between the thumb control and piston 84. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston.

In another preferred embodiment constructed in accordance with the present invention, two or more puller wires (not shown) are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90° from the first, i.e., a first curve in one plane generally along the axis of the tip section before it is deflected and a second curve distal to the first curve in a plane transverse, and preferably normal to the first plane. The high torque characteristic of the catheter tip section 12 reduces the tendency for the deflection in one direction to deform the deflection in the other direction. Suitable deflection control handles for use with such a catheter are described in U.S. Pat. Nos. 6,123,699, 6,171,277, 6,183,463, and 6,468,260, the disclosures of which are incorporated herein by reference.

As an alternative to the above described embodiment, the puller wires (not shown) may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body.

The preceding description has been presented with reference to presently preferred embodiments of the invention. Workers skilled in the art and technology to which this invention pertains will appreciate that alterations and changes in the described structure may be practiced without meaningful departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

The invention claimed is:

1. An injection catheter comprising:
a catheter body comprising an outer wall, proximal and distal ends and at least one lumen therethrough;
a tip section comprising a flexible tubing having proximal and distal ends, wherein the proximal end of the tip section is mounted at the distal end of the catheter body;
a needle control handle at the proximal end of the catheter body;
an injection needle comprising elongated tubing extending through the tip section, catheter body, and needle control handle and having a proximal end attached to the needle control handle, the injection needle also having a distal region within the tip section and an open distal end, wherein the injection needle is longitudinally slidable within the tip section so that its distal region can extend beyond the distal end of the tip section upon suitable manipulation of the needle control handle, and further wherein the distal region of the injection needle has four fluid ports along its length in addition to the open distal end of the needle, wherein a first pair of fluid ports is positioned on one side of the injection needle and a second-pair of fluid ports is positioned on an opposite side of the injection needle, wherein each pair of fluid ports includes a distal-most fluid port and a proximal-most fluid port, the distal-most fluid port of each pair of fluid ports being positioned about two inches from the distal end of the injection needle, and the proximal-most fluid port of each pair of fluid ports being distanced about 0.02 inches from its corresponding distal-most fluid port;
a protective tube mounted coaxially around the injection needle;
whereby, in use, fluid passes out of the needle through the open distal end of the needle and through the fluid ports along the length of the distal region.

2. An injection catheter according to claim 1, wherein the fluid ports are round.

3. An injection catheter according to claim 1, wherein the fluid ports are oval.

4. An injection catheter according to claim 1, wherein the fluid ports are rectangular.

5. An injection catheter according to claim 1, wherein the fluid ports comprise horizontal slots.

6. An injection catheter according to claim 1, wherein the fluid ports comprise vertical slots.

7. An injection catheter according to claim 1, wherein the tip section comprises a tip electrode mounted on the distal end of the tip section, wherein the injection needle extends through the tip electrode.

8. An injection catheter comprising:
a catheter body comprising a flexible tubing having proximal and distal ends and at least one lumen therethrough;
a tip section comprising a flexible tubing having proximal and distal ends, wherein the proximal end of the tip section is mounted at the distal end of the catheter body;
a tip electrode mounted on the distal end of the tip section;
a needle control handle at the proximal end of the catheter body;
an injection needle comprising elongated tubing extending through the catheter body, tip section and needle control handle and having a proximal end attached to the needle control handle, the injection needle also having a distal region within the tip section and an open distal end, wherein the injection needle is longitudinally slidable within the catheter body so that its distal region can extend beyond the distal end of the tip section upon suitable manipulation of the needle control handle, and further wherein the distal region of the injection needle has four fluid ports along its length in addition to the open distal end of the needle, wherein a first pair of fluid ports is positioned on one side of the injection needle and a second-pair of fluid ports is positioned on an opposite side of the injection needle, wherein each pair of fluid ports includes a distal-most fluid port and a proximal-most fluid port, the distal-most fluid port of each pair of fluid ports being positioned about two inches from the distal end of the injection needle, and the proximal-most fluid port of each pair of fluid ports being distanced about 0.02 inches from its corresponding distal-most fluid port;
a protective tube mounted coaxially around the injection needle; and
an electromagnetic location sensor mounted in the distal end of the tip section;
whereby, in use, fluid passes out of the needle through the open distal end of the needle and through the fluid ports along the length of the distal region.

9. An injection catheter according to claim 8, wherein the fluid ports are round.

10. An injection catheter according to claim 8, wherein the fluid ports are oval.

11. An injection catheter according to claim 8, wherein the fluid ports are rectangular.

12. An injection catheter according to claim 8, wherein the fluid ports comprise horizontal slots.

13. An injection catheter according to claim 8, wherein the fluid ports comprise vertical slots.

14. An injection catheter according to claim 8, wherein the injection needle extends through the tip electrode.

15. An injection catheter according to claim 8, further comprising at least one ring electrode.

16. An injection catheter according to claim 1, further comprising at least one ring electrode.

17. An injection catheter according to claim 1, wherein the protective tube is adapted to provide a fluid tight seal surrounding the injection needle.

18. An injection catheter according to claim 8, wherein the protective tube is adapted to provide a fluid tight seal surrounding the injection needle.

19. An injection catheter comprising:
- a catheter body comprising an outer wall, proximal and distal ends and at least one lumen therethrough;
- a tip section comprising a flexible tubing having proximal and distal ends, wherein the proximal end of the tip section is mounted at the distal end of the catheter body;
- a needle control handle at the proximal end of the catheter body;
- an injection needle comprising elongated tubing extending through the tip section, catheter body, and needle control handle and having a proximal end attached to the needle control handle, the injection needle also having a distal region within the tip section and an open distal end, wherein the injection needle is longitudinally slidable within the tip section so that its distal region can extend beyond the distal end of the tip section upon suitable manipulation of the needle control handle, and further wherein the distal region of the injection needle has four fluid ports along its length in addition to the open distal end of the needle, wherein a first pair of fluid ports is positioned on one side of the injection needle and a second-pair of fluid ports is positioned on an opposite side of the injection needle, wherein each pair of fluid ports includes a distal-most fluid port and a proximal-most fluid port;
- a protective tube mounted coaxially around the injection needle;
- whereby, in use, fluid passes out of the needle through the open distal end of the needle and through the fluid ports along the length of the distal region.

* * * * *